United States Patent [19]

Ogiu et al.

[11] Patent Number: 4,706,654
[45] Date of Patent: Nov. 17, 1987

[54] ENDOSCOPE HAVING INTERNAL PRESSURE COMMUNICATION MEANS

[75] Inventors: Hisao Ogiu; Haruhiko Kaiya, both of Tokyo, Japan

[73] Assignee: Olympus Optical Co., Ltd., Tokyo, Japan

[21] Appl. No.: 893,235

[22] Filed: Aug. 5, 1986

[30] Foreign Application Priority Data

Aug. 16, 1985 [JP] Japan ................... 60-180218
Dec. 6, 1985 [JP] Japan ............... 60-188080[U]

[51] Int. Cl.$^4$ ............................................... A61B 1/00
[52] U.S. Cl. ................................................... 128/4
[58] Field of Search ........................... 128/4, 6, 3, 5, 7

[56] References Cited

U.S. PATENT DOCUMENTS

| | | | |
|---|---|---|---|
| 4,216,767 | 8/1980 | Aoshiro | 128/6 |
| 4,240,411 | 12/1980 | Hosono | 128/4 |
| 4,241,729 | 12/1980 | Aoshiro | 128/4 |
| 4,419,987 | 12/1983 | Ogiu | 128/4 |
| 4,491,865 | 1/1985 | Danna et al. | 358/98 |
| 4,537,209 | 8/1985 | Sasa | 128/4 X |
| 4,574,783 | 3/1986 | Kazuhiro et al. | 128/4 |
| 4,641,635 | 2/1987 | Yabe | 128/6 |

*Primary Examiner*—William H. Grieb

[57] ABSTRACT

An endoscope includes an operation section and an insertion section extending from the operation section. An image-pickup unit is disposed in the extended end portion of the insertion section. The unit has an objective optical system, a solid-state image-pickup device, and a case accommodating the optical system and image-pickup device. The interior of the case communicates with the interior of the endoscope.

10 Claims, 11 Drawing Figures

F I G. 4A
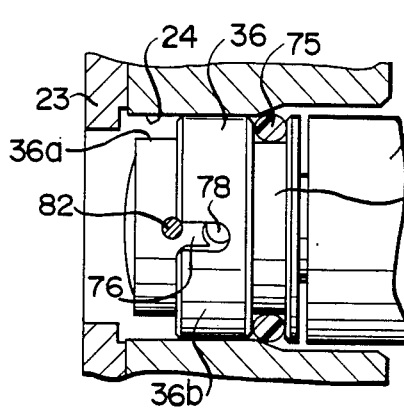
F I G. 4B
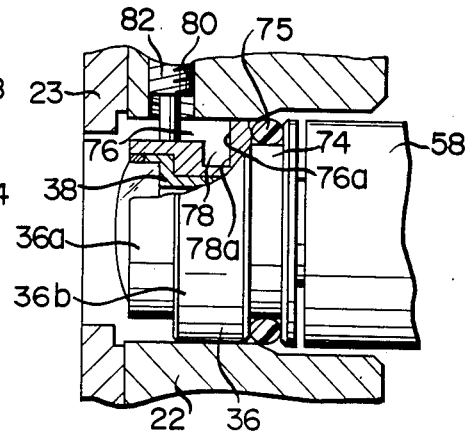
F I G. 5A
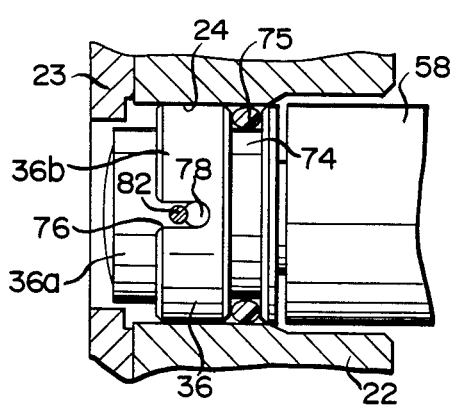
F I G. 5B
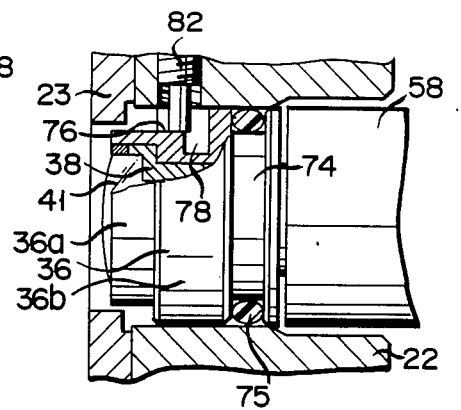

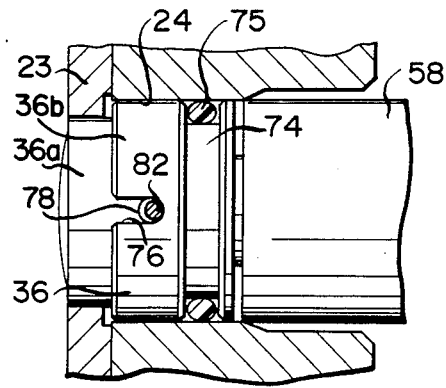
F I G. 6A
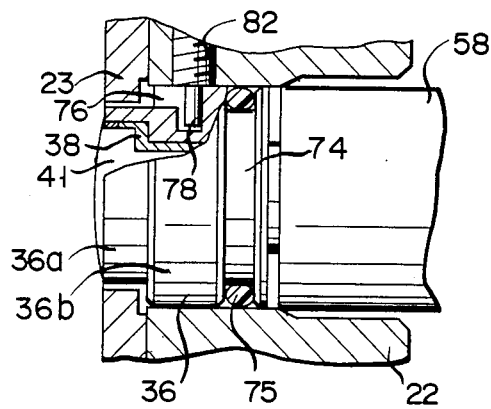
F I G. 6B
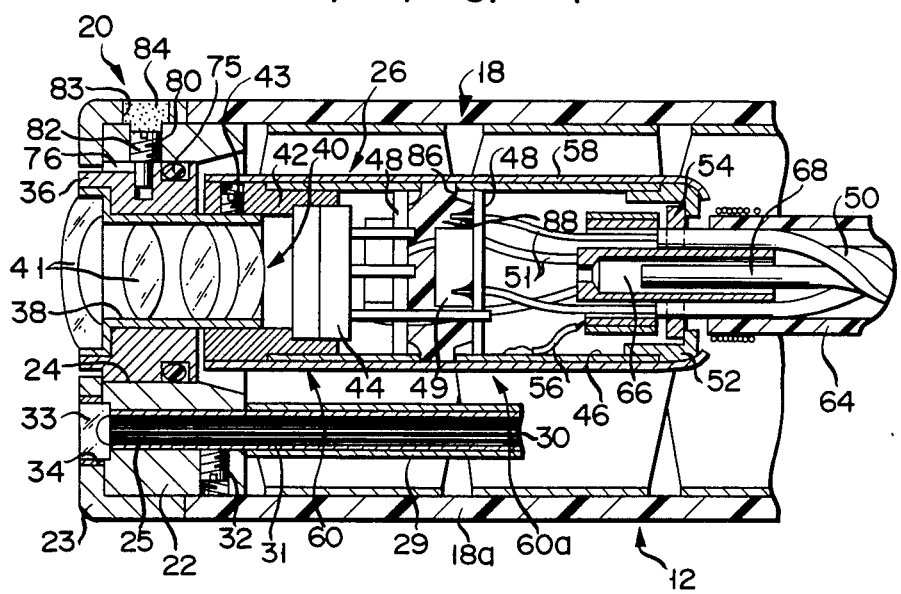
F I G. 7

ENDOSCOPE HAVING INTERNAL PRESSURE COMMUNICATION MEANS

BACKGROUND OF THE INVENTION

The present invention relates to an electronic image-pickup type endoscope which comprises an image-pickup unit including an objective optical system, a solid-state image-pickup device, and electronic components associated therewith.

Multifunctional electronic endoscopes have recently been developed. In a conventional electronic endoscope, an optical image is picked up using a solid-state image-pickup device, such as a CCD (Charge-Coupled Device), and observed on a monitor. This type of endoscope includes an image-pickup unit having a solid-state image-pickup device and electronic components associated therewith. The unit is accommodated in a sealed case. The case is arranged inside the endoscope.

Endoscopes are normally sterilized with a gas such as ethylene oxide gas. During sterilization, the endoscope is maintained in a reduced-pressure environment. In order to prevent the outer case of the endoscope from exploding, the interior of the endoscope is also evacuated. However, since the case accommodating the image-pickup unit is sealed, a pressure difference occurs between the case interior and the endoscope interior upon evacuation of the latter. When gas sterilization is repeatedly performed, a decrease in strength at the adhered portions of the image-pickup device and the case, and hence peeling thereof, tend to occur. In addition, when a portion is shielded with a conductive adhesive, this results in incomplete conduction, thus degrading the shielding effect.

The above problems are also encountered when endoscopes are transported by air. When an aircraft reaches high altitude, the ambient and internal pressures of endoscopes are reduced, thereby causing the above phenomenon.

SUMMARY OF THE INVENTION

The present invention has been developed in consideration of the above situation, and has as its object to provide an endoscope wherein damage to the adhered portions, a decrease in adhesion strength, and incomplete conduction of an image-pickup unit can be prevented, even when the internal pressure of the endoscope is reduced during gas sterilization or transportation by air.

In order to achieve the above object of the present invention, there is provided an endoscope wherein the interior of a case accommodating an image-pickup unit communicates with the interior of the endoscope, so that the internal pressure of the endoscope coincides with the internal pressure of the case. For this reason, no pressure difference between the interior of the endoscope and the interior of the case occurs during transportation by air or during gas sterilization.

BRIEF DESCRIPTION OF THE DRAWINGS

FIGS. 1 to 6B show an endoscope according to an embodiment of the present invention, in which FIG. 1 is a sectional view showing the overall arrangement of the endoscope, FIG. 2 is a sectional view of the distal end of the insertion section of the endoscope, and FIGS. 3A to 6B are views for explaining the assembly process of an image-pickup unit into the distal end of the insertion section, in which FIGS. 3A, 4A, 5A, and 6A are partially cutaway plan views thereof, and FIGS. 3B, 4B, 5B, and 6B are partially cutaway side views thereof; and FIG. 7 is a sectional view corresponding to FIG. 2, showing a modification of the present invention.

DETAILED DESCRIPTION OF THE PREFERRED EMBODIMENT

An endoscope according to an embodiment of the present invention will now be described with reference to the accompanying drawings.

Figure 1:
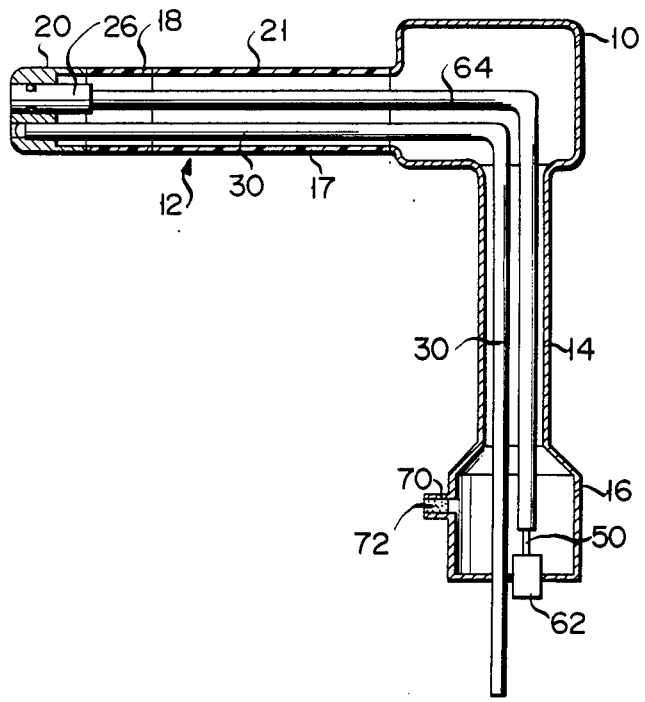

Referring to FIG. 1, the endoscope comprises operation section 10, insertion section 12 extending from operation section 10, for insertion in a body cavity, and a universal cord 14 extending from section 10. Connector 16 is mounted at the extending end of cord 14. Insertion section 12 includes flexible pipe 17 extending from operation section 10, bendable portion 18, and distal end assembly 20. The endoscope as a whole is covered by case 21 to constitute a liquid-tight structure.

Figure 2:
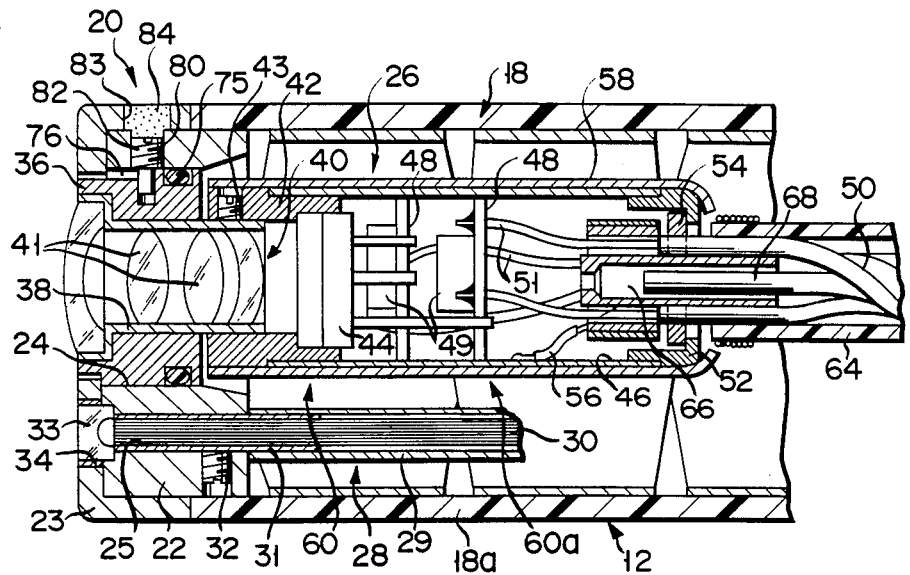

Referring to FIG. 2, assembly 20 comprises metal body 22, and distal end cover 23 made of an electricity-insulating material and covering the outer surface of metal body 22. Assembly 20 has the same diameter as sheath 18a of bendable portion 18. A pair of through holes 24 and 25 are formed in assembly 20 and extend along the axial direction of insertion section 12. Image-pickup unit 26 (to be described in detail later) is arranged in through hole 24, and illumination optical system 28 is arranged in through hole 25. In assembly 20 are formed other through holes (not shown) for a forceps channel and a liquid/air supply channel. Optical system 28 includes light guide fibers 30 covered by tube 29. Metal sleeve 31 is fitted on the outer surface of the distal end portion of the fibers. Sleeve 31 is inserted in through hole 25 and is fastened by fastening screw 32 screwed in body 22 from the outside thereof. Illumination lens 33 is fixed by adhesive to the distal end of fibers 30. Lens 33 is located in opening 34 formed in cover 23. Fibers 30 extend to connector 16 through insertion section 12, operation section 10, and universal cord 14.

Image-pickup unit 26 comprises substantially cylindrical insulating frame 36 made of an electricity-insulating material. Frame 36 has substantially the same outer diameter as the diameter of through hole 24 and is fitted therein. Cylindrical lens frame 38 made of metal is inserted in frame 36 and fixed by adhesive. Frame 36 and lens frame 38 are kept liquid-tight. A plurality of objective lenses 41 constituting objective optical system 40 are mounted in lens frame 38. The rear end portion of lens frame 38 extends outward from insulating frame 36. The rear end portion is electrically and liquid-tightly connected to cylindrical element frame 42, made of metal. More specifically, element frame 42 is fixed by set screw 43 to lens frame 38. Screw 43 is screwed from the outside to lens frame 38. Solid-state image-pickup device 44 is fixed by adhesive in element frame 42 and located opposite objective optical system 40. Metal shield pipe 46 is fixed by adhesive on the outer surface of element frame 42 and extends backward from the element frame. A pair of circuit boards 48 are fixed inside shield pipe 46 and oppose image-pickup device 44. The leads of device 44 are soldered to boards 48. Various electronic components 49 constituting an electric circuit associated with the image-pickup device are arranged on the circuit boards. Core wires 51 of signal transmission coaxial cable 50 are connected to boards 48. The distal end of cable 50 is mounted on wire-fixing member 54. This fixing member is fixed to the rear end of shield pipe 46 through mounting frame 52. One end of shield wire 56 of cable 50 is soldered to fixing member 54, and the other end is soldered to shield pipe 46. The outer surfaces of element frame 42, shield pipe 46, and mounting frame 52 are covered with insulating member 58. Insulating frame 36, lens frame 38, element frame 42, shield pipe 46, mounting frame 52, and insulating member 58 constitute case 60 of image-pickup unit 26. In particular, element frame 42, shield pipe 46, mounting frame 52, and insulating member 58 constitute shield case 60a for shielding solid-state image-pickup device 44 and circuit boards 48 having electronic components 49 thereon.

As shown in FIGS. 1 and 2, coaxial cable 50 extends from wire-fixing member 54 to connector 16 through insertion section 12, operation section 10, and universal cord 14. The rear end of cable 50 is connected to connecting terminal 62 arranged in connector 16. Protective tube 64 is loosely fitted on cable 50. The distal end of tube 64 is connected to wire-fixing member 54, and the rear end of tube 64 is open inside connector 16, i.e., inside the endoscope. As shown in FIG. 2, communication hole 66 is formed in wire-fixing member 54 and communicates with the interior of case 60 in image-pickup unit 26 and with protective tube 64. Therefore, the interior of case 60 communicates with the interior of the endoscope through hole 66 and tube 64. The distal end portion of noise cancellation wire 68 extending together with cable 50 is inserted in hole 66.

Vent port 70 is formed in the wall of connector 16. Vent material 72 is filled in port 70 to allow permeation of a sterilization gas such as ethylene oxide, but does not allow permeation of liquid. Thus, the interior of the endoscope can communicate with the outer atmosphere.

Figure 3A:
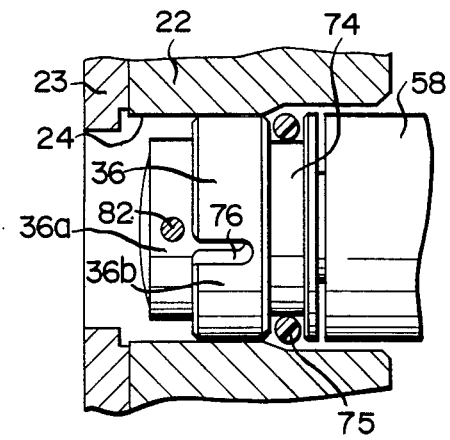

As shown in FIGS. 2 and 3A, insulating frame 36 of image-pickup unit 26 has small-diameter portion 36a located at the front side thereof and large-diamater portion 36b located at the rear side thereof. Annular groove 74 is formed on the outer surface of large-diameter portion 36b, and O-ring 75 is fitted in groove 74. O-ring 75 is in air-tight contact with the inner surface of through hole 24 formed in distal end assembly 20. Guide groove 76 is formed at a portion in large-diameter portion 36b corresponding to the upper portion of device 44. Groove 76 extends along the axial direction of insulating frame 36 from the intermediate portion to the distal end of large-diameter portion 36b. The distal end of groove 76 is open at the end face of large-diameter portion 36b. The edge of groove 76 is chamfered. Fixing hole 78 deeper than the guide groove is formed in the bottom surface of the rear end portion of guide groove 76. Rear end face 78a of fixing hole 78 coincides with rear end face 76a of guide groove 76 (FIG. 4B). Screw hole 80 extending along the radial direction of body 22 in assembly 20 is formed therein at a portion opposite guide groove 76 and fixing hole 78. Through hole 83 is formed in cover 23 and communicates with screw hole 80. Fastening screw 82 is threadably engaged with hole 80 from the outside of cover 23 to the inside thereof. The distal end portion of screw 82 is inserted in fixing hole 78 in insulating frame 36. Image-pickup unit 26 is fixed to distal end assembly 20 by screw 82. Potting material 84 is potted and sealed in through hole 83.

The assembly of image-pickup unit 26 having the structure described above, and the incorporation of unit 26 into distal end assembly 20 will now be described.

Figure 3B:
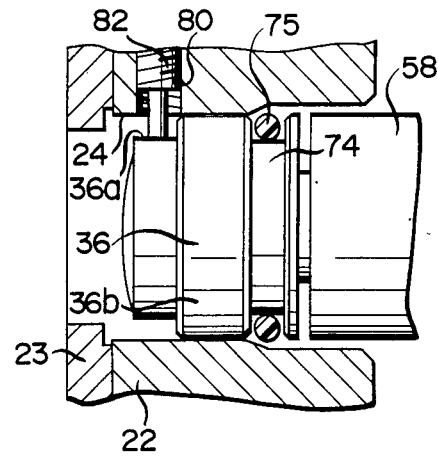

When element frame 42, bonded and fixed to image-pickup device 44 in advance, is bonded and fixed to insulating frame 36 and then mounted on lens frame 78, frame 42 is fitted on the outer surface of the rear end portion of frame 38. Device 44 has vertical directionality. For this reason, when frame 42 is mounted on frame 38, the upper direction of device 44 must be located at fixing hole 78 of insulating frame 36, at a predetermined angle, such that the upper direction of the observed image produced by device 44 is aligned with the upper direction of distal end assembly 20. At the same time, focusing operation of device 44 with respect to objective lens system 40 is performed. After positioning of device 44 with respect to insulating frame 36 and lens frame 38 is completed, element frame 42 is fixed by screw 43 to lens frame 38. Subsequently, O-ring 75 is fitted in annular groove 74 in insulating frame 36. After or before illumination optical system 28 is incorporated in distal end assembly 20, unit 26 is incorporated in assembly 20. Incorporation of unit 26 into assembly 20 is performed in the following manner:

As shown in FIGS. 3A and 3B, insulating frame 36, located at the distal end of unit 26, is inserted up to the intermediate portion of through hole 24. In this case, small-diameter portion 36a of frame 36 is inserted first. Screw 82 is threadably engaged in hole 80 formed in assembly 20, so that screw 82 is brought into contact with the outer surface of small-diameter portion 36a. In this state, as shown in FIGS. 4A and 4B, image-pickup unit 26 is further inserted until the end face of large-diameter portion 36b abuts against screw 82. Subsequently, unit 26 is pivoted to fit screw 82 into guide groove 76. As shown in FIGS. 5A and 5B, unit 26 is moved forward along groove 76 by using screw 82 as a guide member. As shown in FIGS. 6A and 6B, unit 26 is moved forward until rear end face 76a of guide groove 76 abuts against screw 82. Rear end face 76a of the guide groove is aligned with rear end face 78a of fixing hole 78, so that hole 78 opposes screw 82. In this state, when screw 82 is screwed in, its distal end is inserted in the fixing hole. Thus, image-pickup unit 26 is liquid-tightly fixed to distal end assembly 20 through O-ring 75. Finally, potting material 84 is filled in through hole 83, thereby liquid-tightly sealing screw hole 80.

If image-pickup unit 26 needs to be repaired or replaced with a new unit, screw 82 is loosened and removed from fixing hole 78. The image-pickup unit is then pulled backward and removed from assembly 20.

The endoscope having the arrangement described above has the following advantages:

During endoscope transportation by air or during gas sterilization, when the endoscope is placed in a reduced-pressure environment, the interior of the endoscope is also evacuated through vent port 70. The interior of shield case 60a in unit 26 communicates with the interior of the endoscope through communication hole 66 and protective tube 64, thereby evacuating the interior of the shield case. Therefore, no pressure difference occurs between the interior of the endoscope and the interior of shield case 60a. The adhered portions of the shield case are neither damaged nor peeled. In addition, a portion shielded with a conductive adhesive is free from incomplete conduction.

Fastening screw 82 is screwed into distal end assembly 20, and guide groove 76, engaged with the fastening screw, is formed in image-pickup unit 26. At the same time, fixing hole 78 is formed in the rear end portion of the guide groove. For this reason, when unit 26 is to be inserted in assembly 20, guide groove 76 is engaged with fastening screw 82, so that screw 82 can be used as a guide for inserting the image-pickup unit to a predetermined position of the distal end assembly. As a result, alignment of image-pickup unit 26 with respect to distal end assembly 20 and incorporation thereof can be easily performed with high accuracy. If guide groove 76 is not formed in image-pickup unit 26 but fixing hole 78 is formed therein, the fixing hole cannot be visually checked from the outside of the distal end assembly. Therefore, it is difficult to align the fastening screw with the fixing hole, and the operator must perform the alignment manually. It then takes a long period of time to incorporate image-pickup unit 26 in the distal end assembly.

According to this embodiment, fastening screw 82 and guide groove 76 cooperate to simplify alignment of image-pickup unit 26 with distal end assembly 20.

The present invention is not limited to the particular embodiment described above. Various changes and modifications may be made within the spirit and scope of the invention.

FIG. 7 shows a modification of the distal end of the insertion section of the endoscope. In this modification, injection hole 86 is formed in shield pipe 46. Filler 88 is injected into the shield pipe from injection hole 86 before insulating member 58 covers the outer surface of shield pipe 46. Circuit boards 48 and electronic components 49 are covered with the filler. Filler 88 is preferably an electricity-insulating material which absorbs vibrations and may be exemplified by silicone resin or the like.

According to this modification, even if an impact such as vibration acts on the endoscope, damage to the electric circuit portion and short-circuiting of the electric circuit by humidity can be prevented.

In the above embodiment, the interior of the image-pickup unit can communicate with the interior of the endoscope through the communication hole and the protective tube. However, the interior of the image-pickup unit can directly communicate with the interior of the endoscope without going through the protective tube. In addition, vent port 70 need not always be formed in connector 16. A vent port may be formed in operation section 10, insertion section 12, or universal cord 14.

What is claimed is:

1. An endoscope comprising:
   an operation section;
   an insertion section extending from said operation section, for insertion in a body cavity, said insertion section being provided with a distal end assembly arranged at an extending end thereof;
   a universal cord extending from said operation section;
   a connector mounted at an extending end of said universal cord; and
   an image-pickup unit arranged in the extended end portion of said insertion section, said image-pickup unit having an objective optical system for forming an optical image, a solid-state image-pickup device for picking up the optical image formed by said objective optical system, and a case accommodating said objective optical system and said image-pickup device, said case being provided with a communication portion for causing the interior of said endoscope to communicate with the interior of said case.

2. An endoscope according to claim 1, wherein said communication portion has a communication hole formed in said case.

3. An endoscope according to claim 2, wherein said image-pickup unit includes a circuit board having a plurality of electronic components connected to said image-pickup device, and an electric cable having one end connected to said circuit board and the other end connected to said connector, said cable extending through the interior of said endoscope, and said case includes a shield pipe which covers said image-pickup device and said circuit board, and a cable-fixing member fixed to said shield pipe and supporting said one end portion of said electric cable, said communication hole being formed in said cable-fixing member.

4. An endoscope according to claim 3, wherein said image-pickup unit has a protective tube loosely receiving said electric cable therein, one end of said protective tube communicating with said communication hole and the other end being open inside said endoscope, near said connector.

5. An endoscope according to claim 3, wherein said image-pickup unit includes a noise cancellation wire extending along said electric cable and having one end portion inserted in said communication hole.

6. An endoscope according to claim 3, wherein said image-pickup unit includes a vibration-damping member which is injected in said shield pipe, surrounds said electronic components, and has an electrical insulation property.

7. An endoscope according to claim 1, wherein said connector includes a vent port communicating with the interior of said endoscope and a vent material filled in said vent port to allow permeation of a gas but not to allow permeation of a liquid.

8. An endoscope according to claim 1, wherein said image-pickup unit includes a substantially cylindrical insulating frame located outside said objective optical system, and a guide groove formed in an outer surface of said insulating frame and axially extending therealong, said guide groove being formed at a predetermined position with respect to said solid-state image-pickup device, and having a rear end located at a solid-state image-pickup device side, and an open front end; and said distal end assembly includes a main body having a through hole into which said insulating frame is inserted, and a fastening screw screwed in said main body to project into said through hole, for engaging with said guide groove to guide insertion of said insulating frame into said through hole and for positioning said image-pickup unit with respect to said distal end assembly.

9. An endoscope according to claim 8, wherein said image-pickup device has vertical directionality, and said guide groove is formed at a position corresponding to the upper direction of said image-pickup device.

10. An endoscope according to claim 8, wherein said insulating frame has a fixing hole formed in the bottom surface of said rear end of said guide groove, the fixing hole being adapted to receive said fastening screw.

* * * * *